United States Patent
Jiang

(10) Patent No.: US 6,539,286 B1
(45) Date of Patent: Mar. 25, 2003

(54) FLUID LEVEL SENSOR

(75) Inventor: Tongbi Jiang, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/013,418

(22) Filed: Jan. 26, 1998

(51) Int. Cl.$^7$ .............................................. G05D 4/00
(52) U.S. Cl. ..................... 700/282; 700/281; 700/283; 73/304 R
(58) Field of Search ............................... 700/282, 283, 700/240, 281; 156/51, 47; 239/63, 65, 68, 69, 99; 73/304 R

(56) References Cited

U.S. PATENT DOCUMENTS

| | | | |
|---|---|---|---|
| 3,617,387 A | * 11/1971 | Grulke et al. ............... 429/162 |
| 4,287,427 A | 9/1981 | Scifres ....................... 250/577 |
| 4,425,795 A | * 1/1984 | Albrecht et al. | |
| 4,428,232 A | 1/1984 | Tanaka et al. ................ 73/304 |
| 4,433,577 A | * 2/1984 | Khurgin et al. | |
| 4,518,956 A | 5/1985 | Kitagawa et al. ........... 340/620 |
| 4,570,230 A | * 2/1986 | Wilson et al. .............. 700/207 |
| 4,573,128 A | * 2/1986 | Mazur ........................ 700/281 |
| 4,592,231 A | 6/1986 | Kant ........................... 73/295 |
| 4,671,110 A | 6/1987 | De Kock ..................... 73/323 |
| 4,739,658 A | 4/1988 | Slavik ......................... 73/313 |
| 4,749,988 A | 6/1988 | Berman et al. ............. 340/618 |
| 4,782,451 A | * 11/1988 | Mazzarella et al. ........ 700/281 |
| 4,788,861 A | * 12/1988 | Lichti ....................... 73/304 R |
| 4,817,277 A | * 4/1989 | Hieber et al. | |
| 4,922,852 A | * 5/1990 | Price ........................... 118/683 |
| 4,938,383 A | * 7/1990 | Yamazaki et al. ............ 222/41 |
| 4,949,069 A | 8/1990 | Wilson ..................... 340/450.1 |
| 4,961,456 A | 10/1990 | Stembridge et al. .......... 141/1 |
| 5,005,005 A | * 4/1991 | Brossia et al. ............... 340/604 |
| 5,005,407 A | * 4/1991 | Koon ....................... 73/290 R |
| 5,078,010 A | * 1/1992 | Lock ........................ 73/304 R |
| 5,121,631 A | * 6/1992 | Koon ....................... 73/290 R |
| 5,134,248 A | * 7/1992 | Kiec et al. ................ 174/84 R |
| 5,150,037 A | 9/1992 | Kouzuki ..................... 324/71.4 |
| 5,182,947 A | 2/1993 | Fidelak et al. ................ 73/304 |
| 5,210,769 A | 5/1993 | Seidel et al. .................. 73/295 |
| 5,291,031 A | 3/1994 | Mac Donald et al. ....... 250/577 |
| 5,498,490 A | * 3/1996 | Brodd ........................ 429/149 |
| 5,583,544 A | 12/1996 | Stamer et al. .................. 347/7 |
| 5,600,285 A | * 2/1997 | Sachs et al. .................... 333/1 |
| 5,626,053 A | * 5/1997 | Williamson ............... 73/304 R |
| 5,668,536 A | * 9/1997 | Gottshall et al. .......... 73/304 R |
| 5,681,757 A | * 10/1997 | Hayes ......................... 257/778 |
| 5,686,703 A | * 11/1997 | Yamaguchi | |
| 5,686,829 A | 11/1997 | Girault ........................ 324/72 |
| 5,687,092 A | 11/1997 | Bretmersky et al. ........ 702/100 |
| 5,742,500 A | * 4/1998 | Irvin ............................. 700/9 |
| 5,782,410 A | * 7/1998 | Weston ........................ 239/63 |
| 5,825,526 A | * 10/1998 | Bommarito et al. ........ 359/265 |
| 5,837,892 A | * 11/1998 | Cavallaro et al. ............ 73/149 |
| 5,847,929 A | * 12/1998 | Bernier et al. ............. 361/719 |
| 5,904,500 A | * 5/1999 | Tay ............................ 438/118 |
| 5,907,266 A | * 5/1999 | Budka et al. ............... 333/116 |
| 5,912,759 A | * 6/1999 | Good et al. ................. 359/297 |
| 5,938,386 A | * 8/1999 | Remerowski et al. ......... 411/82 |
| 5,941,843 A | * 8/1999 | Atanasoska et al. .......... 604/20 |
| 5,971,227 A | * 10/1999 | White et al. ................. 222/333 |
| 5,988,859 A | * 11/1999 | Kirk ........................... 700/232 |
| 5,995,909 A | * 11/1999 | Bretmersky et al. .......... 702/50 |

* cited by examiner

*Primary Examiner*—Paul P. Gordon
(74) *Attorney, Agent, or Firm*—Trop, Pruner & Hu, P.C.

(57) ABSTRACT

A fluid level sensor is used in a container in a system for dispensing adhesive used in the formation of electronic devices. The sensor includes a pair of electrical conductors positioned inside the container. A voltage is applied across the conductors to cause a current flow through the fluid in the container. The magnitude of the current flow represents the amount of fluid remaining in the container. If an empty container is detected, the system is shut off.

34 Claims, 3 Drawing Sheets

FLUID LEVEL SENSOR

BACKGROUND

The invention relates to a fluid level sensor positioned in a container that dispenses fluid used in forming electronic devices.

In the exemplary manufacturing process of electronic devices, different types of materials are used. For example, adhesives are commonly used to attach one component of a device to another component. To make an integrated circuit device, a die is mounted to a support structure by means of adhesives, which can be one of several types, including metal alloys (e.g., solder) and organic or inorganic adhesives (e.g., epoxies and polyimides, which can be filled with metal).

In the integrated circuit device 10 shown in FIG. 1, a die 14 can be mounted to a leadframe 12 by using an adhesive layer 16 to attach the underside 34 of the die 14 to the top surface 30 of leadframe 12. If an epoxy or polyimide type adhesive is used, the adhesive is typically dispensed in fluid form onto portions of the top surface 30 of the leadframe 12. After formation of the adhesive layer 16, the die 14 is contacted to the adhesive layer 16 to bond the die 14 to the leadframe 12. Next, bond pads 24 on the die 14 are wirebonded (using wires 26) to corresponding bond pads 22 on leadfingers 20 of the leadframe 12. The leadframe/die assembly is then encapsulated using an encapsulant 18 (e.g., plastic).

An adhesive originally in fluid form is dispensed onto a target support structure, such as the leadframe 12 in FIG. 1, using a dispensing container in a die attach machine. Various automated methods have been used to detect the level of the fluid adhesive inside the dispensing container. One method that has been used is magnetic sensing. The dispensing container includes a ferromagnetic coated piston that sits on top of the fluid adhesive. As the adhesive is being dispensed, the level of the fluid decreases, and the ferromagnetic piston falls inside the cylindrical container with the fluid level. When the ferromagnetic coated piston reaches a predetermined position in the container, it activates a magnetic sensor to stop the die attach machine. However, certain types of adhesives contain ferromagnetic fillers that may interfere with the magnetic sensing mechanism.

Various fluid level sensors and detectors have been proposed to detect different types of fluid (e.g., gasoline, water, oil) stored in different types of containers. Such sensors include optical sensors and electrical sensors.

SUMMARY

Generally, the invention is directed to a sensor used in a fluid dispensing container, the sensor including a pair of electrical conductors positioned in the dispensing container to which a voltage to detect the amount of fluid in the container.

The invention has one or more of the following advantages. Accurate sensing of the fluid level in a fluid dispensing container can be performed with a large variety of adhesives, including adhesives filled with a ferromagnetic filler. The fluid level sensing can be accomplished without the use of moving parts inside the container, which improves reliability and facilitates handling.

In general, in one aspect, the invention features a system for dispensing an adhesive onto an electronic device. The system includes a container storing the adhesive and a port through which the adhesive can flow. Electronic conductors are positioned in the container. A voltage is applied across the conductors so that a current flow is induced through the adhesive in the container. The current is measured to determine a level of the adhesive in the container.

In general, in another aspect, the invention features a method of applying an adhesive onto an electronic device. The adhesive is stored in a container having electrical conductors positioned in the container. A voltage is applied across the conductors. The current flow through the adhesive is measured to determine the adhesive level in the container. The adhesive is supplied to the electronic device until the adhesive level drops below a predetermined amount.

Other features and advantages will become apparent from the following description and from the claims.

DETAILED DESCRIPTION

Figure 2:
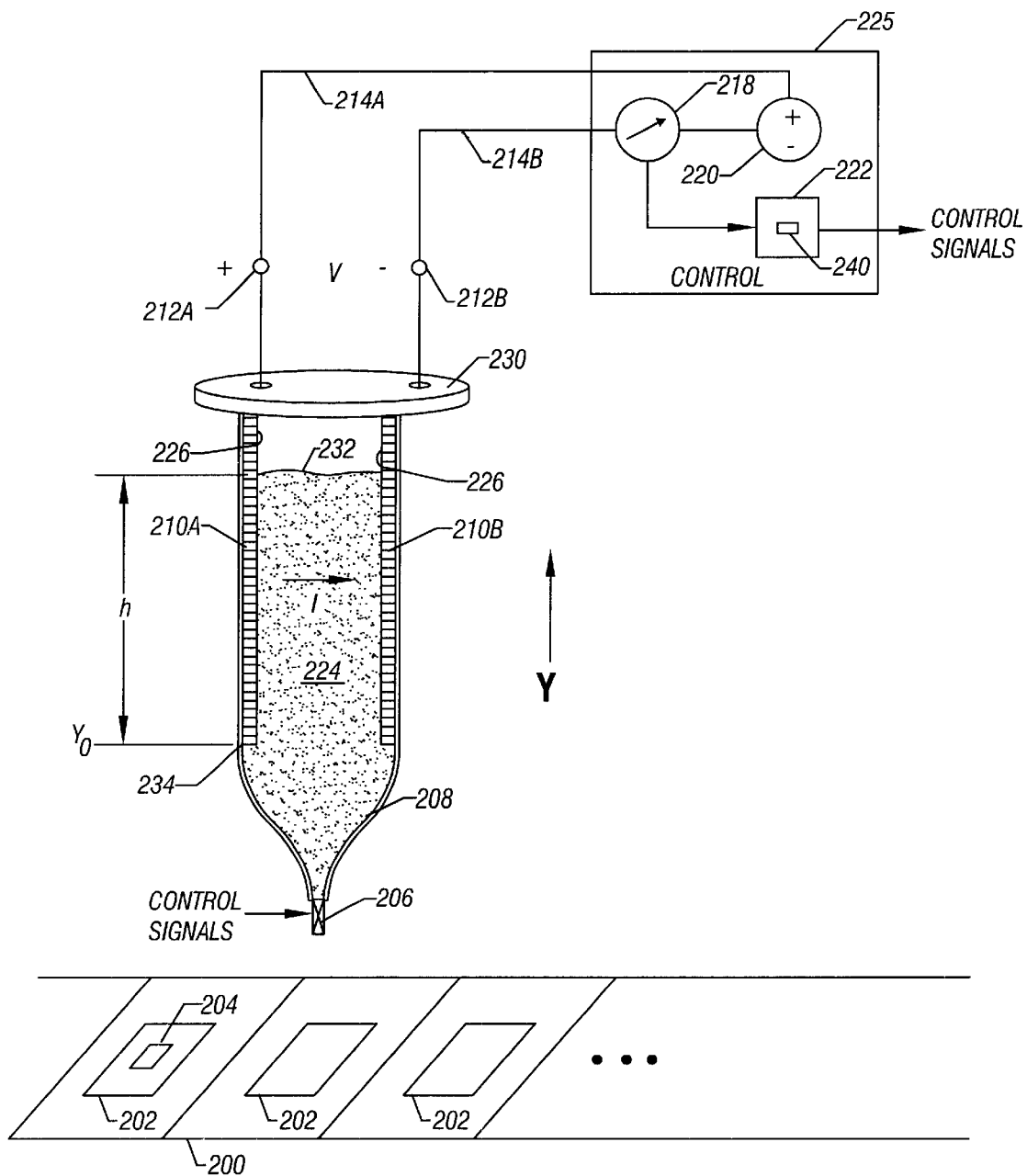
FIG. 2 is a diagram of an adhesive dispensing container having a fluid level sensor according to the invention.

Referring to FIG. 2, a fluid dispensing container 208 (e.g., a syringe) contains an adhesive 224 in fluid form. The adhesive 224 can be made of various materials, including organic or inorganic adhesives such as thermoset or thermoplastic compounds (e.g., epoxies and polyimides) or some mixture of such compounds. The adhesive can be filled with such electrically conductive fillers as gold (Au), silver (Ag), nickel (Ni), or nickel-plated polystyrene. Nickel and nickel-plated polystyrene (which are ferromagnetic fillers) are examples of fillers used in epoxies or polyimides that may interfere with a fluid level sensing system that is based on magnetic sensing. The ferromagnetic fillers may inadvertently activate the magnetic sensor to cause a false empty indication.

In the electrical sensing system used in the adhesive dispensing container 208 shown in FIG. 2, however, numerous types of electrically conductive adhesives can be used, including adhesives that are filled with a ferromagnetic filler. The fluid dispensing container 208 includes two strips of electrical conductors placed along the inner wall 226 in the longitudinal or vertical direction Y of the dispensing container 208. The conductors 210A and 210B can be formed of any electrically conductive material, such as copper, gold, silver, or a tungsten coated material.

The conductors 210A and 210B can be coated to the inner wall 226 of the container 208, or the conductors can be removable probes inserted into the container 208.

The conductors 210A and 210B extend from the top 230 of the container 208 and run to a predetermined depth into the container 208. The electrically-conductive, fluid adhesive 224 is dispensed through a nozzle 206 under control of control signals provided by a controller 222 in a control block 225. The controller 222 can selectively activate or deactivate the assembly line 200 and notify operators of the container empty condition. Adhesive layers 204 can be formed on target electronic structures 202 (e.g., wafers, leadframes, printed wiring boards, and other integrated circuit or packaged devices). The adhesive layers 204 can later be subjected to a high temperature curing process to bond a die to a support structure, for example.

To detect current flow through the fluid adhesive 224, a voltage V is applied across electrodes 212A and 212B connected to the conductors 210A and 210B, respectively, in the container 208. The electrodes 212A and 212B are connected by lines 214A and 214B, respectively, to a voltage source 220 that is programmable to control the voltage V across electrodes 212A and 212B. A current meter 218 is connected to detect the current flow through the circuit formed by the voltage source 220, electrodes 212A, 212B, conductors 210A, 210B and the fluid adhesive 224.

From the voltage V and current I, the resistance R of the fluid adhesive 224 can be determined. For a predefined type of adhesive material, a threshold resistance value is stored in a memory 240 in the controller 222. The measured resistance is compared to the threshold resistance to determine whether or not to shut off the line 200.

Certain types of adhesives are more conductive then others. For the less conductive adhesives, a higher voltage V can be applied across the electrodes 212A and 212B to increase current flow through the adhesive 224. For highly conductive adhesives, the current V is decreased to decrease the current flow I.

Figure 1:
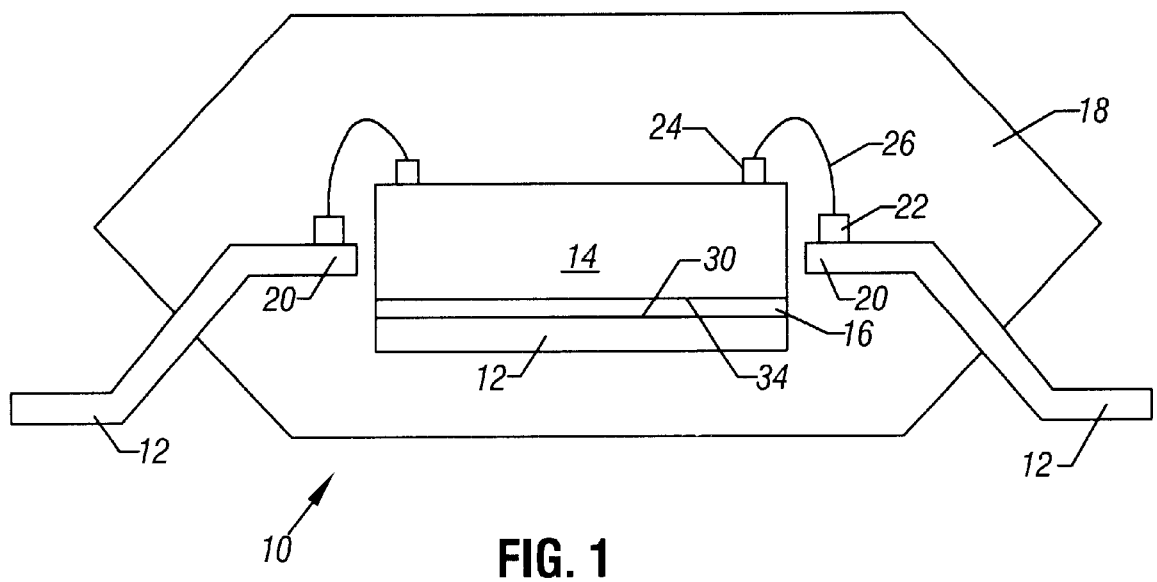
FIG. 1 is an enlarged, cross-sectional view of a prior art integrated circuit device.
Figure 3:
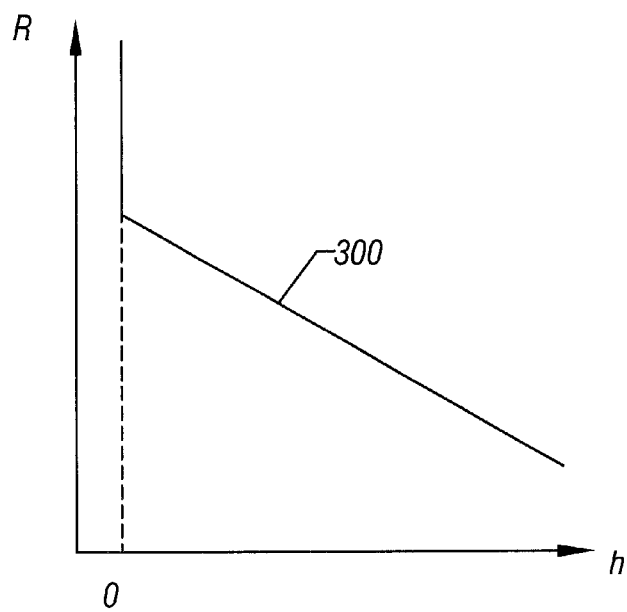
FIG. 3 is a graph showing resistance of the adhesive in the adhesive dispensing container with respect to the level of the adhesive in the container.

Referring to FIG. 3, a graph shows the resistance R through the adhesive 224 as a function of the level of the adhesive in the container 208, as measured by the height h of the adhesive 224 from an initial position $Y_0$ along the Y direction. The resistance R increases generally linearly with a decrease in the height h of the adhesive 224. When the adhesive level 232 drops below the position $Y_0$, (i.e., the fluid level drops below the bottom edge of the conductors 210A and 210B), the resistance R rises sharply to infinity.

Figure 4:
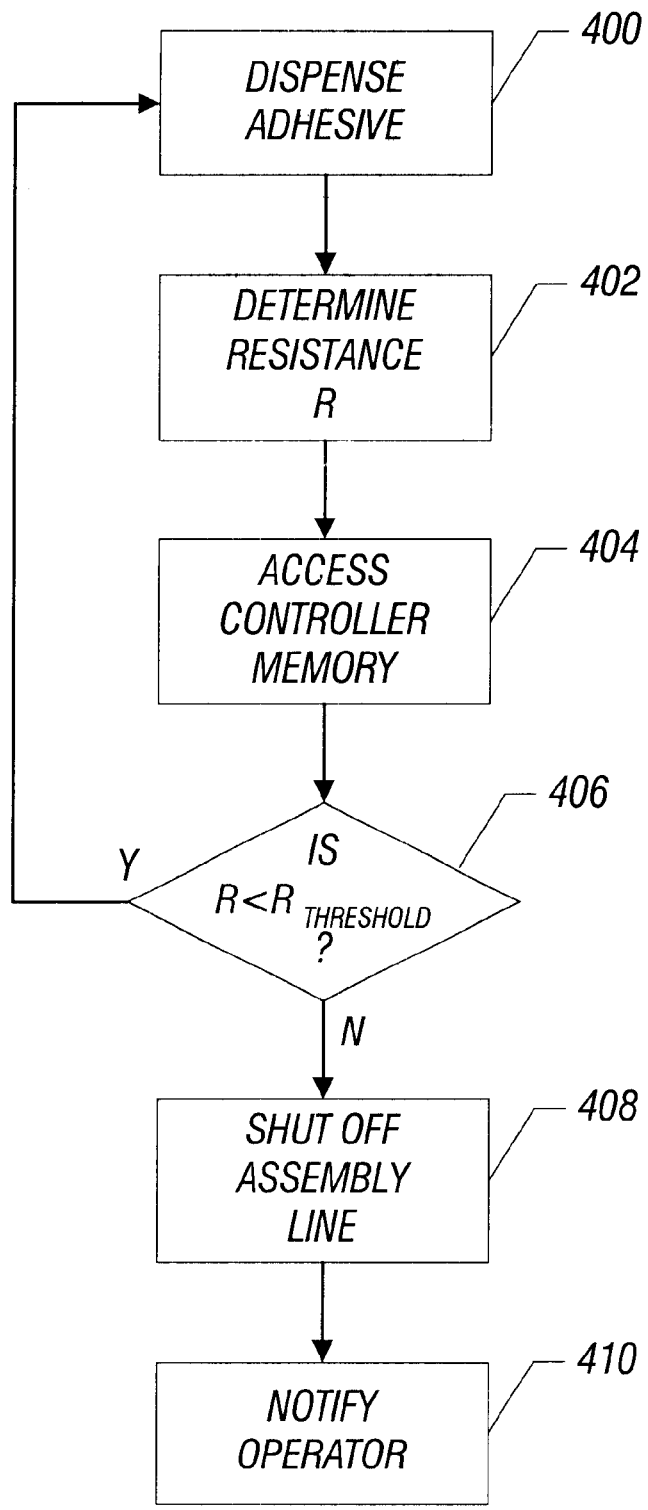
FIG. 4 is a flow diagram of the process for dispensing adhesive onto electronic devices.

Referring to FIG. 4, the flow of a portion of the controller 222 is illustrated. During the die attach operation, the controller 222 causes the nozzle 206 of the container 208 to dispense adhesive onto target structures 202 on the assembly line 200 (step 400). Next, based upon the applied voltage V and the detected current I, the resistance R representing the amount of adhesive 224 in the container 208 is determined (step 402). The controller 222 then accesses the controller memory 240 to obtain a threshold resistance $R_{threshold}$ that is based on the type of adhesive material used (step 404). The detected resistance R is then compared to the threshold resistance $R_{threshold}$ (step 406). If the measured resistance R is less than $R_{threshold}$, then the die attaching system remains on and the dispenser 208 continues to dispense adhesive (step 400). However, if R is not less than $R_{threshold}$, then the container 208 is considered empty and the nozzle 206 is shut off and the line is temporarily stopped (step 408) by setting control signals from the controller 222 to appropriate states. The operator is then notified of the empty container condition (step 410).

Other embodiments are within the scope of the following claims. For example, although the fluid level sensor has been described in conjunction with sensing the level of an adhesive in a container, the levels of other fluids can also be similarly detected. Other configurations of the electrical conductors in the container can be used. Instead of long strips of conductors, smaller electrodes can be positioned at a predetermined depth inside the container. Using such electrodes, current flow will occur until the fluid level drops below the electrodes, at which point the current will sharply decrease.

What is claimed is:

1. A method of applying an adhesive onto an electronic device, the method comprising:
    storing the adhesive in a container having electrical conductors positioned inside the container;
    applying a voltage across the conductors;
    measuring current flow through the adhesive to determine the adhesive level in the container; and
    supplying the adhesive to the electronic device until the adhesive level drops below a predetermined amount.

2. The method of claim 1, wherein storing the adhesive comprises storing an electrically conductive adhesive in the container.

3. The method of claim 1, wherein storing the adhesive in the container having electrical conductors positioned inside the container comprises storing the adhesive in the container having electrical conductors, wherein each of the conductors contains a material selected from the group consisting of copper, gold, silver, and tungsten.

4. The method of claim 1, wherein storing the adhesive comprises storing the adhesive comprising electronically conductive fillers.

5. The method of claim 4, wherein storing the adhesive comprises storing the adhesive comprising filler material containing nickel.

6. The method of claim 4, wherein storing the adhesive comprises storing the adhesive comprising filler material containing gold.

7. The method of claim 4, wherein storing the adhesive comprises storing the adhesive comprising filler material containing silver.

8. The method of claim 1, wherein applying a voltage across the conductors comprises applying a varying voltage across the conductors.

9. The method of claim 1, further comprising:
    determining a resistance value based on the applied voltage and measured current.

10. The method of claim 9, further comprising:
    comparing the determined resistance to a threshold resistance to determine if the container is empty.

11. The method of claim 1, wherein applying the voltage comprises applying a voltage based on a conductivity of the adhesive.

12. The method of claim 1, wherein storing comprises storing the adhesive in the container having the electrical conductors coated on an inside wall of the container.

13. The method of claim 1, comprising supplying the adhesive until the adhesive level drops below the predetermined amount, wherein the predetermined amount is based on the measured current.

14. A system for dispensing an adhesive onto an electronic device, comprising:
    a container adapted to store the adhesive and a port through which the adhesive can flow;
    electrical conductors positioned inside the container; and
    a controller adapted to apply a voltage across the electrical conductors, wherein a current is induced through the adhesive, the current being measured to determine a level of the adhesive in the container and to supply the adhesive to the electronic device based on the measured current.

15. The system of claim 14, wherein the current decreases with the amount of adhesive adapted to be stored in the container.

16. The system of claim 14, wherein a voltage is applied across the electrical conductors.

17. The system of claim 14, wherein each of the conductors contains a material selected from the group consisting of copper, gold, silver, and tungsten.

18. The system of claim 14, wherein the electrical conductors comprise a first conductor and a second conductor, and wherein the first and second conductors are of substantially same length.

19. The system of claim 14, wherein the adhesive is dispensed onto a leadframe in the electronic device.

20. The system of claim 14, wherein the adhesive flow is stopped when the detected adhesive level drops below a predetermined level.

21. The apparatus of claim 14, wherein the controller compares a determined resistance to a threshold resistance to determine if more adhesive is desired.

22. Apparatus for detecting a level of an adhesive inside a container, comprising:
   electrical conductors positioned inside the container;
   a controller electrically coupled to the electrical conductors to apply a voltage to the conductors;
   a measurement device configured to measure current flow through the adhesive capable of being stored inside the container to determine the adhesive level and a port to provide the adhesive to a device until the measured current is a preselected value.

23. The apparatus of claim 22, wherein each of the electrical conductors is coated to a corresponding inner wall of the container.

24. The apparatus of claim 22, wherein the electrical conductors include probes placed inside the container.

25. The apparatus of claim 22, wherein the adhesive is electrically conductive.

26. The apparatus of claim 25, wherein the adhesive contains an electronically conductive filler.

27. The apparatus of claim 22, wherein the adhesive includes a material selected from a group consisting of a thermoset compound, a thermoplastic compound, and a mixture of thermoset and thermoplastic compounds.

28. The apparatus of claim 22, wherein the controller applies the voltage based on a conductivity of the adhesive.

29. The apparatus of claim 22, wherein the controller determines a resistance value based on the applied voltage and measured current.

30. A method, comprising:
   allowing application of a voltage across electrical conductors positioned inside a container capable of storing an adhesive;
   enabling measuring current flow through the adhesive to determine a adhesive level in the container; and
   enabling supplying the adhesive to an electronic device in response to measuring the current flow through the adhesive.

31. The method of claim 30, wherein enabling supplying the adhesive to the electronic device in response to measuring the current flow comprises enabling supplying the adhesive to the electronic device until the adhesive level drops below a predetermined amount.

32. The method of claim 30, further comprising enabling determining a resistance value based on the applied voltage and measured current.

33. The method of claim 32, further comprising enabling comparison of the determined resistance to a threshold resistance to determine if the container is empty.

34. An apparatus comprising:
   conductors positioned inside a container;
   a controller communicatively coupled to the conductors to apply a voltage to the conductor; and
   a device to detect presence of current through an adhesive inside the container to determine a level of the adhesive and to supply the adhesive to a device based on the determined adhesive level.

* * * * *